United States Patent [19]

Bauer et al.

[11] Patent Number: 4,828,589
[45] Date of Patent: May 9, 1989

[54] FILTER UNIT WITH APPARATUS FOR DETERMINING THE SATURATION OF A DRYING CARTRIDGE

[75] Inventors: Heinz Bauer, Munich; Jens Piening, Socking, both of Fed. Rep. of Germany

[73] Assignee: Bauer-Kompressoren Heinz Bauer, Munich, Fed. Rep. of Germany

[21] Appl. No.: 125,409

[22] Filed: Nov. 25, 1987

Related U.S. Application Data

[63] Continuation of Ser. No. 370,988, Apr. 22, 1982, abandoned, and a continuation-in-part of Ser. No. 792,434, Oct. 29, 1985, abandoned.

[30] Foreign Application Priority Data

May 15, 1981 [EP] European Pat. Off. .......... 8110373.3

[51] Int. Cl.$^4$ .............................................. B01D 53/04
[52] U.S. Cl. ...................................... 55/217; 55/275; 55/387; 361/286
[58] Field of Search ............................. 55/20, 31–33, 55/35, 74, 75, 160–163, 179, 208, 217, 270, 275, 387; 361/286, 433 R, 433 S, 306, 308, 309, 433 H, 433 T

[56] References Cited

U.S. PATENT DOCUMENTS

| | | | |
|---|---|---|---|
| 1,715,560 | 6/1929 | Menut | 361/306 |
| 2,266,114 | 12/1941 | Bartlett | 361/286 X |
| 2,396,474 | 3/1946 | Riley | 55/208 X |
| 2,471,442 | 5/1949 | Morf | 55/208 |
| 2,703,628 | 3/1955 | Pompeo et al. | 55/179 X |
| 2,758,149 | 8/1956 | Brennan | 361/433 H X |
| 2,904,751 | 9/1959 | Parsons | 361/286 X |
| 3,142,830 | 7/1964 | Patrick et al. | 55/275 |
| 3,243,674 | 3/1966 | Ebert | 361/286 X |
| 3,246,216 | 4/1966 | Mead et al. | 361/286 |
| 3,424,977 | 1/1969 | Krobath | 361/286 X |
| 3,448,561 | 6/1969 | Seibert et al. | 55/20 |
| 3,715,866 | 2/1973 | Chatlos et al. | 55/275 X |
| 4,127,395 | 11/1978 | McKey et al. | 55/20 |
| 4,278,453 | 7/1981 | Klein | 55/275 |
| 4,351,649 | 9/1982 | Owens et al. | 55/275 X |
| 4,552,570 | 11/1985 | Gravatt | 55/179 X |

FOREIGN PATENT DOCUMENTS

| | | | |
|---|---|---|---|
| 1123479 | 9/1956 | France | 361/281 |
| 1210765 | 3/1960 | France | 361/433 T |

*Primary Examiner*—Robert Spitzer
*Attorney, Agent, or Firm*—Gifford, Groh, Sheridan, Sprinkle and Dolgorukov

[57] ABSTRACT

An apparatus for determining the degree of water saturation of the hygroscopic desiccant of a disposable drying cartridge as a function of the variation in the dielectric constant of the hygroscopic material. The invention takes the form of a tubular capacitor disposed in the mass of hygroscopic desiccant material proximate the outlet of the drying cartridge, and of appropriate circuits for measuring the level of saturation of the desiccant material and for operating alarm and safety devices. A removable plug provides access to the cartridge mounted in a casing. The plug has a pair of electrical contacts acting to biasing position the cartridge in the casing and provide effective electrical contact with the capacitor.

9 Claims, 2 Drawing Sheets

FILTER UNIT WITH APPARATUS FOR DETERMINING THE SATURATION OF A DRYING CARTRIDGE

CROSS REFERENCE TO RELATED APPLICATIONS

This application is a continuation-in-part of the prior application Ser. No. 792,434 filed Oct. 29, 1985, now abandoned, which is a continuation of application Ser. No. 370,988, filed Apr. 22, 1982, now abandoned.

BACKGROUND OF THE INVENTION

1. Field of the Invention

The present invention relates to a filter unit having a replaceable cartridge having an apparatus for determining the saturation level of a filtering cartridge filled with hygroscopic desiccant granular material which is used for drying gases containing water vapor, and more particularly for compressed breathable air.

2. Prior Art

In producing compressed gases, particularly compressed air, it is necessary to dry the gas. Drying is usually achieved by circulating a gas through a drying element containing hygroscopic desiccant material which removes any moisture. Hygroscopic desiccant granular material, for example aluminum oxide, generally changes gradually from a physically dry state to a partially dry state, which still permits the desiccant to extract water from the gas, and then changes very rapidly to a saturated state beyond which further extraction of moisture from the gas is no longer possible.

During operation of a drying element in a circuit through which flows a gas which must be dried, the level of moisture absorbed by the particles of hygroscopic desiccant material must be carefully monitored to avoid full saturation of the particles and thus prevent further adsorption of moisture from the gas. When the desiccant material must be purged or replaced, the drying elements must be replaced or purged prior to reaching the full moisture saturation point or level of the hygroscopic desiccant material.

In order to take no risk, the drying elements must be replaced or purged long before the desiccant has reached a full saturation level, in order to meet the most elementary safety regulations. Such a procedure is understandably not optimal and leads to economic waste, as drying elements or cartridges cannot be used to their full potential capacity thus causing an unnecessary high consumption and frequent changes of the drying elements, and frequent shutdowns of the system due to frequent changeover of drying cartridges.

It is known to measure the absorption of a desiccant dryer as a function of the capacitance of a capacitor such as disclosed in U.S. Pat. No. 4,552,570.

SUMMARY OF THE INVENTION

The present invention accomplishes its objects, presenting advantages over filter units of the prior art, by providing a structure for a filter unit having a casing carrying a disposable drying filter cartridge. The cartridge has a first electrode embedded in a mass of hygroscopic desiccant material and an internal surface which is at least partially electrically conductive. The electrode and internal surface form a capacitor. The saturation degree of the hygroscopic material can be ascertained by the change of capacitance in comparison with predetermined reference values.

The casing has an end plug removable from the casing for replacing the cartridge. The end plug has an electrically conductive biasing member for positioning the casing and for delivering electrical current to said internal surface of said cartridges. A pin extends from the end cap to electrically contact the electrode of the casing. A monitoring, measuring and control circuit is located outside of the housing and electrically connected to said end cap to monitor the change in capacitance of the capacitor and determine the saturation of the cartridge.

The electrodes of the cartridge are positioned in the vicinity of an outlet of the cartridge. This is because the hygroscopic desiccant particles contained within the housing become progressively saturated from an inlet, where the heavily water saturated gas, such as air, flows into the cartridge, to the "dry gas" outlet. In other words, it is only necessary to measure the degree of saturation of about five percent of the particles proximate to the outlet, and it is not necessary to measure the degree of saturation of the remaining ninety five percent of the particles which have been previously fully saturated. It is only when those five percent of the particles, i.e. those particles situated proximate to the outlet, become saturated that the element needs to be replaced.

In order to obtain precise measurements, it is advantageous to have a capacitor which is subjected to a wide change in capacitance when the desiccant particles become saturated. It is also advantageous to provide the electrodes with a shape similar to that of the filter cartridge housing. It was experimentally discovered that both the electrode and the filter cartridge housing should preferably be cylindrical in shape, such as to form a cylindrical capacitor.

It has been further discovered that the electrical current flowing through the drying element, that is to say across the capacitor, can be directly used as the signal representing the degree of saturation, when displayed on an appropriate instrument such as a meter. By way of an appropriate utilization circuit, the gas compressor such as an air compressor, can be shut off when the saturation point is reached. With such an arrangement, air compressor systems can be controlled without human intervention.

The invention further contemplates comparing the capacitance of a capacitor built in a filter drying cartridge with a predetermined reference value and to shut off the power to the gas compressor unless the comparison indicates that such a drying filter is actually installed in the system. Such an arrangement provides a safety feature that prevents the compressor from being operated when a drying filter cartridge has not been installed.

Applicant further discloses cutting off the flow of gas through the dryer when an adsorbent has become saturated and drying the adsorbent by introducing a purge gas through the adsorbent to remove the moisture from the adsorbent. However, such a method requires a relatively complicated apparatus to introduce the purged gas through the adsorbent. This arrangement is not only complicated and cumbersome, but not well suited for many applications, particularly portable compressed air units.

Therefore, it is an object of this invention to provide a simple, inexpensive filter unit which has a capacitor formed in an adsorbent to provide an indication of saturation of the adsorbent.

It is a further object of this invention to provide a filter unit having a replaceable drying cartridge having a capacitor for measuring the saturation of the adsorbent in the drying cartridge.

It is yet another object of the invention to provide a filter unit having a removable cap member biased against a replaceable cartridge.

It is yet another object of the invention to provide a filter unit having a cover plate having a pair of electrical contacts biasingly connected to an electrode and inner surface of a replaceable drying cartridge.

The many objects and advantages of the present invention will be apparent to those skilled in the art when the following description of the best mode contemplated for practicing the invention is read in conjunction with the drawing wherein like reference numerals refer to like and equivalent elements, and in which:

DETAILED DESCRIPTION OF THE PREFERRED EMBODIMENT

Figure 3:
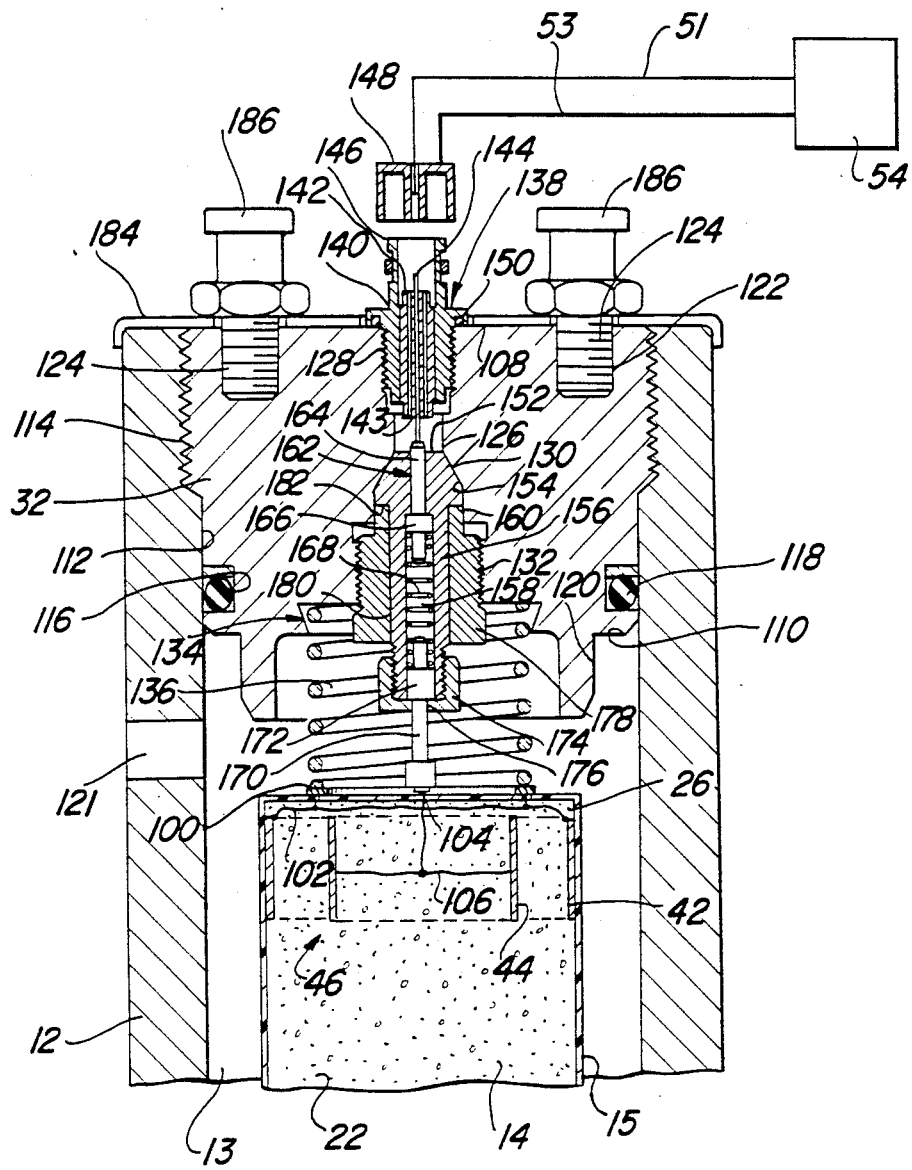
FIG. 3 is a sectional view of a preferred embodiment of a filter unit according to the invention.

A filter unit 110 according to the invention is shown in FIG. 3, where there is shown a tubular cylindrical casing 12 having a central bore 13 adapted to receive a drying cartridge 14. One end of the cylindrical casing 12 is closed by plug 16 (FIG. 1) which is threaded into the casing. An inlet 18 (FIG. 1) is formed through the plug 16 for admitting, through a line (not shown), moist compressed air into the bore.

Positioned within the bore 13 of the casing 12 in abuttment with the plug 16 is the drying cartridge 14. The drying cartridge is self-contained and may be removed and changed as desired. The drying cartridge 14 has a housing 15 formed of any suitable dielectric material such as plastic. The housing 15 is a solid cylinder having a perforate end wall 24 (FIG. 1) adjacent the inlet 18 of the casing and a perforate outlet wall 26 at an other end of the cartridge 14. Contained inside the housing 15 is a mass of hygroscopic desiccant material 22 such as aluminum oxide particles, for example. The perforate end wall 24 affords a passage for moist air from the inlet 18 to the desiccant material of the cartridge.

A preferred embodiment of the invention is shown in FIG. 3. An outlet 121 for exhausting gas dried by the drying cartridge extends through the casing 12. The outlet 121 is positioned adjacent to outlet wall 26 of the cartridge 14.

A cylindrical metallic coating is fixed to an inner surface of the housing to form a first electrode 42. The first electrode 42 is positioned adjacent the outlet wall 26 of the cartridge. A second cylindrical electrode 44 is embedded in the mass of hygroscopic desiccant material 22 concentrically with respect to the first electrode 42 on the internal wall of the cartridge housing 15. The concentric electrodes 42 and 44 form a capacitor 46.

An annular metallic ring 100 is affixed to the exterior of the outlet wall 26 of the cartridge and connected to the first electrode by a wire 102. A metal contact 104 is mounted concentrically with respect to the ring 100 on the outlet end 26 and connected to electrode 44 by wire 106.

A cylindrical plug 32 is removably mounted in an other end of the tubular casing 12. The plug 32 has an outer end 108 and an inner end 110 with a side wall 112 extending therebetween. The side wall 112 has a threaded portion 114 extending from the outer end for threadably engaging the casing 12. An annular groove 116 extends about the side wall 112 adjacent the inner end surface for accepting an O-ring gasket 118. The O-ring gasket 118 provides an airtight seal between the plug 32 and the casing. A pair of threaded bores 122 extend into the outer end 108 to accept threaded studs 124. Extending outwardly from the inner end 110 is an annular cylindrical wall 120. A center bore 126 extends from the outer end 108 through the plug to the inner end 110 concentric with the annular cylindrical wall 120. The center bore has a first threaded surface 128 adjacent the outer end, a frustoconical surface 130 and a second threaded surface 132 adjacent the inner end of the plug. A groove 134 having a frustoconical side wall is formed in the inner end of the plug concentric with the annular cylindrical wall 120. The groove 134 is concentric with the bore and is formed to retain a spring 136 for a purpose as set forth more fully below.

A female connector 138 is threadably engaged in the first threaded surface of the center bore. The female connector has an outer annular portion 140 electrically insulated by a non-conducting member 142 from a center conductor 144. The outer portion 140 is formed of electrically conductive material and makes electrical contact with the plug 32. The outer annular portion 140 has an end portion 146 adapted to be interconnected with a male connector 148. The male connector is suitable for rapid connection and disconnection. The center conductor 144 extends axially into the center bore of the casing. An O-ring gasket 150 is interposed between the female connector and the plug to provide a seal.

A cylindrical insulating member 152 having a frustoconical end surface 154 adapted to mate with the frustoconical surface 130 of the center bore 126 is positioned therein. The frustoconical end surface 154 provides an excellent seal when the insulating member 152 is subjected to air pressure from within the bore of the casing. Extending downwardly from the frustoconical end surface 154 of the insulating member 152 is a cylinder 156 having a central opening 158 and a threaded lower end. An annular surface 160 extends outwardly between the cylinder 156 and a bottom side of the frustoconical surface. A hole 162 having a diameter smaller than the central opening 158 extends upwardly through the frustoconical end surface 154 to accept a first electrically conducting rod 164 having an annular collar 166 to engage the insulating member 152. The first rod 164 extends upwardly through the hole 162 to engage the central conductor 144 of the female connector 138. A spring 168 is positioned within the central opening 158 to extend between the annular collar 166 and a second rod 170. The second rod 170 extends from the central opening adjacent the threaded end. The second rod has an annular collar 172 for engaging the spring and retention by a plastic end cap 174. The plastic end cap 174 has a center hole 176 and is threadably engaged on the threaded end portion of the insulating member to retain the second rod 170 within the central opening. The spring 136, first rod 164 and the second rod 170 are formed of electrically conductive material and are electrically connected to the central conductor 144 of the female connector 138. However, the insulating member 152 and end cap 174 are formed of non-conductive material and act to provide a first electrical branch insulated from a second electrical branch formed by the plug 32, outer annular portion 140 of the female connector and the spring 136. The second rod is movable axially within the center opening and biased downwardly by the spring to engage the contact 104 of the cartridge for electrical contact.

A nut 178 having a center aperture 180 adapted to receive the cylinder 156 of the insulating member is threaded into the second threaded surface 132 of the bore of the casing. An end surface 182 of the nut engages the annular surface 160 of the insulating member to retain the insulating member 152 within the bore 126.

The spring 136 extends downwardly from the groove, to engage the annular ring 100 of the cartridge. The second rod 170 moves upwardly and the spring 136 is compressed between the plug 32 and the cartridge when the plug is threaded into the casing. The compression of the spring and the biasing force on the second rod act to maintain good electrical contact between the spring and the second rod as well as biasing the cartridge into position within the bore 26 and to hold the cartridge against the air pressure flowing through the cartridge.

A non-conductive cover plate 184 having holes to accept the pair of studs 124 and the female connector 138 is mounted to the outer end of the plug. The cover plate 184 extends across the outer end of the plug and the end of the casing. Each of a pair of nuts 186 is threaded onto the studs to hold the cover plate in position.

The male connector 148 is electrically connected to the female connector 138 to connect the capacitor 46 to a monitoring, measuring and control circuit 54 by a pair of electrical connectors 51 and 53.

Figure 2:
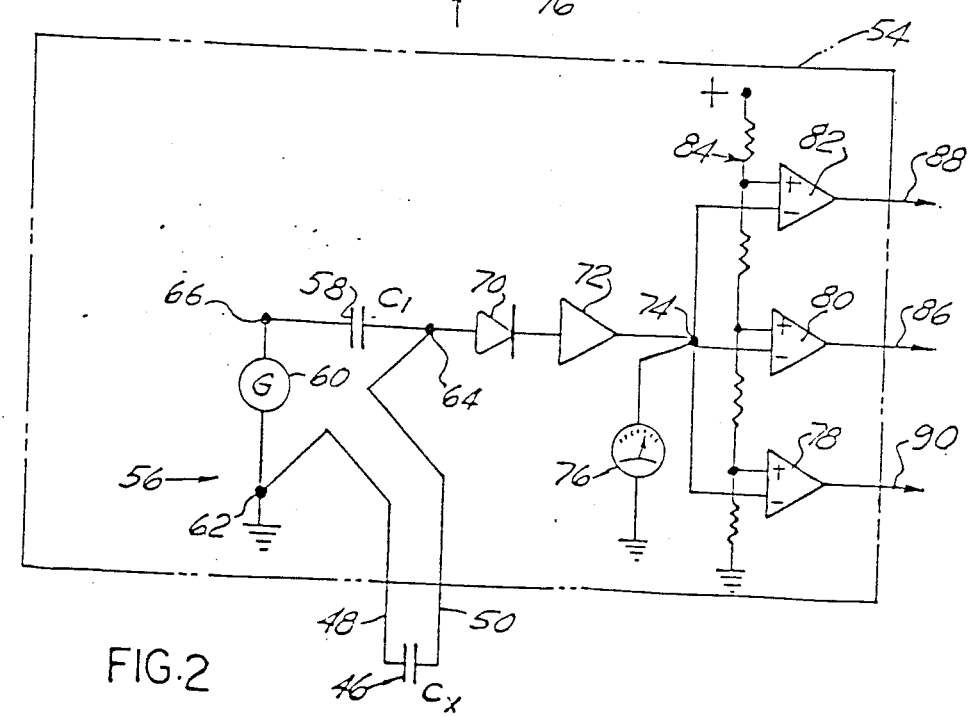
FIG. 2 is an example of monitoring, measuring and control circuit for use in combination with a drying cartridge according to the present invention.

The monitoring, measuring and control circuit 54, schematically illustrated at FIG. 2, comprises at its input a capacitive voltage divider, generally designated at 56. The capacitive voltage divider 56 includes a first branch in which is connected the capacitor 46 of unknown capacitance Cx through the connectors, and a second branch in which is connected a capacitor 58 of known capacitance Cl. A pulse or AC voltage generator 60 is connected between the capacitors 46 and 58. It is known that capacitive voltage dividers such as the capacitive voltage divider 56, permit determination of the value of a capacitance which is unknown, such as the capacitance CX of the capacitor 46, by determining the impedance RcX of the unknown capacitor according to the formula $$Vcx/Vg = Rcx/(Rcl + Rcx),$$

wherein Vcx is the voltage drop across the unknown capacitor 46, i.e. between the points 62 and 64, Vg is the voltage across the generator 60, i.e. between the points 62 and 66, Rcx is the impedance of the capacitor 46 and Rcl is the impedance of the known capacitor 58. Consequently, the unknown capacitance Cx of the capacitor 46 is constantly compared in the circuit 56 to the known capacitance Cl of the capacitor 58, and a voltage signal representative of the unknown capacitance Cx of the capacitor 46 appears across the points, or terminals 62 and 64.

The voltage signal, appearing across the terminals 62 and 64, after rectification through a rectifier circuit symbolically represented by a diode 70, is amplified by a DC amplifier 72 and applied to a common terminal 74. The voltage at the common terminal 74 may be used in several manners. For example, if the voltage is measured by a voltmeter 76, a visual display is obtained which, after proper calibration, gives an indication of the capacitance of the capacitor 46, therefore an indication of the degree of saturation of the hygroscopic desiccant particles 22 in the drying cartridge 14 of FIG. 3.

The voltage at the common terminal 74 is applied to a plurality of comparators, three of which are illustrated at 78, 80 and 82, by being connected to one of the terminals of each comparator. The other terminal of each comparator 78, 80 and 82 is supplied a reference voltage from a voltage divider, designated generally at 84, such that there appears a signal at the output of each comparator, which results from comparing the appropriate reference voltage with the voltage appearing at the common terminal 47. The voltage across the voltage divider 84 is obtained from the same source as that supplying the pulse or AC generator 60, such that the circuit 54 operates independently of the exact voltage across the voltage source, not shown.

The cascade of comparators 78–82 may be arranged such that a signal appears at the output 88 of the comparator 82 when the capacitance of the capacitor 46 of drying filter element, resulting in an increase of the dielectric constant of the hygroscopic particles 22 proximate the outlet of the filter cartridge 14, has risen above a predetermined level which is, for example, a warning level. The signal appearing at the output 88 of the comparator 82 may thus be used to turn on a warning light or to operate any other warning signal. The signal appearing at the output 86 of the comparator 80, indicating a higher degree of saturation of the hygroscopic desiccant material in the filter cartridge, may be used to activate a second and more emphatic warning signal indicating, for example, that the drying cartridge should be changed. The signal appearing at the output 90 of the comparator 78, which may be arranged to be representative of the highest permissible level of saturation of the hygroscopic desiccant material, is preferably used as a shut-off signal for actuating a switch to turn off the electrical power supply to the compressor, or for closing a valve interrupting the flow of compressed air at the output of the compressor. The voltage divider 84 may also be arranged in such a way as to produce a signal 88 at the output of the comparator 82 at an appropriately selected, considerably lower capacitance level. Instead of being used as a prewarning signal, the output signal of comparator 82 may be used to shut off the compressor in the event that a filter cartridge has not been installed in the air flow circuit, or that the cartridge is defective due, for example, to not being completely filled with desiccant, or that the monitoring circuit line is cut-off. Alternatively, a fourth comparator may be included for this purpose, thus maintaining the comparator 82 for producing the prewarning signal.

Figure 1:
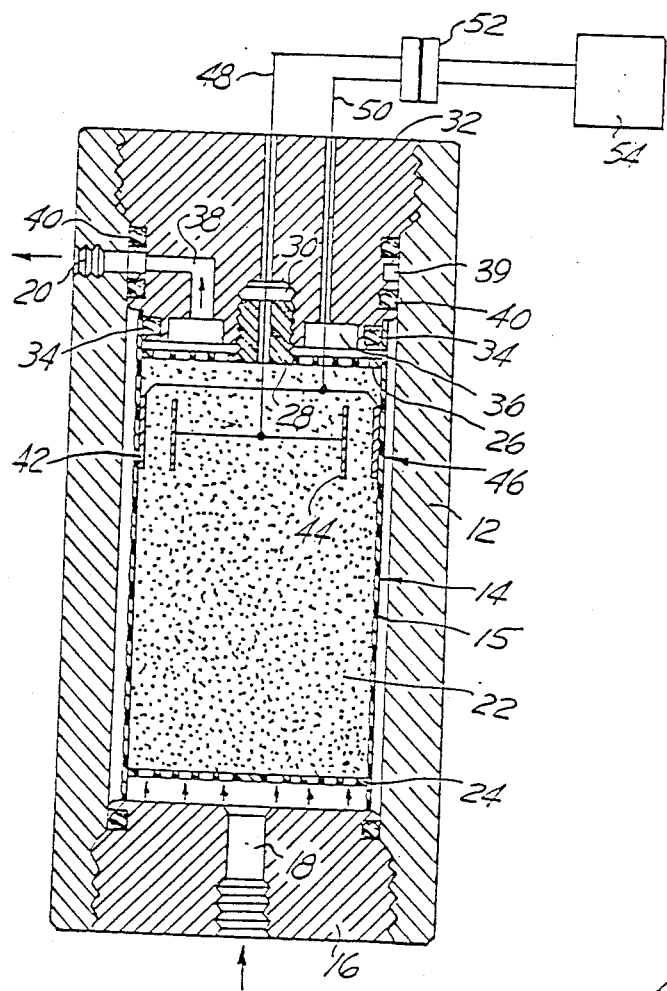
FIG. 1 is a sectional view of an alternative embodiment of a filter unit according to the present invention.

An alternative embodiment is shown in FIG. 1, where the perforate wall 26 is provided with a peripherally threaded nipple 28 engaged in a centrally disposed threaded blind bore 30 formed in a plug 32 threadable in the other end of the tubular casing 12. The cartridge 14 and the plug 32 thus form a replaceable assembly for installation in the tubular casing 12. A seal, such as an O-ring 34, provides a hermetic seal between the periphery of the plug 32 and the outlet end of the cartridge 14. The plug 32 is provided with an annular passageway 36, collecting the dried air passing through the perforate wall 26, and a channel 38 placing the annular passageway 36 in communication with a groove 39 formed on the periphery of the plug 32 and communicating with the lateral outlet 20 in the tubular casing 12. Additional seals, in the form of a pair of O-rings 40, ensure sealing between the periphery of the plug 32 on both sides of the groove 39 and the internal surface of the tubular casing 12. A pair of concentric electrodes 42 and 44 form a capacitor, generally designated 46. The electrodes, or plates, of the capacitor 46 are connected via electrical conductors 48 and 50, respectively, through a connect-disconnect plug 52, to a monitoring, measuring and control circuit 54.

It will be appreciated by those skilled in the art that the example of structure of the drying cartridge hereinbefore described and illustrated at FIGS. 1 and 3 is only an example of structure given for illustrative purpose only. For example, the capacitor 46 may take another form and be, for example, in the conventional form of a capacitor with planar plates.

Having thus described the present invention by way of example of structure adapted to achieve the objects of the invention, modification whereof will be apparent to those skilled in the art, what is claimed as new is as follows:

1. A gas drying filter unit comprising:
   a casing having a bore, said casing further having an inlet and an outlet for flow communication of gas into and out of said bore;
   a replaceable cartridge adapted to be received in said bore, said cartridge having a tubular dielectric housing containing a hygroscopic desiccant material experiencing a variation of electrical dielectric constant as a function of its degree of saturation in moisture, said cartridge further comprising an inlet and an outlet for circulation of said gas through said desiccant material, and a capacitor permanently embedded in said desiccant material proximate said outlet;
   said cartridge further having a pair of electrical contacts mounted thereon, each of said pair of electrical contacts being electrically connected to said capacitor;
   a plug removably mounted to said casing, said plug removable to provide access to said bore for changing said cartridge, said plug having a first electrical biasing contact and a second contact positioned to contact said pair of electrical contacts of said cartridge when said plug is mounted to said casing, said first electrical biasing contact comprising an electrically conductive spring extending between said plug and said cartridge to position said cartridge within said bore; and
   means for determining the level of saturation of said cartridge, said means for determining electrically connected to said first and second contact of said plug to obtain a signal representing capacitance of the capacitance of said capacitor and comparing said capacitance with a plurality of reference values to define a plurality of control signals to determine the level of saturation of said cartridge.

2. The gas drying unit of claim 1, wherein said plug further comprises means for biasing said second electrical contact of said plug.

3. The gas drying unit of claim 1 further comprising means for selectively disconnecting said means for determining the level of saturation from said plug.

4. The gas drying unit of claim 3, wherein said means for selectively disconnecting comprises a first connector member mounted on said plug and a second connector member electrically connected to said means for determining the level of saturation.

5. The gas drying unit of claim 1 wherein said second electrical contact of said plug is concentrically mounted within said first biasing electrical contact of said plug.

6. The gas drying unit of claim 1 wherein said capacitor further comprises a first plate defined by a metallic coating on the interior surface of the dielectric housing of said cartridge and a second plate disposed concentric to said metallic coating in said desiccant material, wherein said plates are disposed such that a portion of said desiccant material is between said plates.

7. The gas drying filter unit of claim 1 further comprising means for applying at least one of said plurality of signals to a visual indicator.

8. The gas drying filter unit of claim 1 further comprising means for applying at least one of said plurality of control signals to an alarm device.

9. The gas drying filter unit of claim 1 further comprising means for applying at least one of said plurality of control signals to means shutting off flow of said gas through said cartridge.

* * * * *